(12) United States Patent
Kirchner et al.

(10) Patent No.: US 8,759,024 B2
(45) Date of Patent: Jun. 24, 2014

(54) PROCESS FOR THE PRODUCTION OF RIBOFLAVIN

(75) Inventors: Florian Kirchner, Tübingen (DE); Klaus Mauch, Stuttgart (DE); Joachim Schmid, Sindelfingen (DE)

(73) Assignee: DSM IP Assets B.V., Heerlen (NL)

( * ) Notice: Subject to any disclaimer, the term of this patent is extended or adjusted under 35 U.S.C. 154(b) by 269 days.

(21) Appl. No.: 13/139,896

(22) PCT Filed: Dec. 15, 2009

(86) PCT No.: PCT/EP2009/008987
§ 371 (c)(1),
(2), (4) Date: Aug. 31, 2011

(87) PCT Pub. No.: WO2010/075960
PCT Pub. Date: Jul. 8, 2010

(65) Prior Publication Data
US 2011/0312026 A1    Dec. 22, 2011

(30) Foreign Application Priority Data
Dec. 15, 2008  (DE) .......................... 10 2008 063 234

(51) Int. Cl.
| C12P 25/00 | (2006.01) |
| C12N 9/00 | (2006.01) |
| C12N 1/20 | (2006.01) |
| C12N 15/00 | (2006.01) |
| C07H 21/04 | (2006.01) |

(52) U.S. Cl.
USPC ....... 435/66; 435/183; 435/252.3; 435/320.1; 536/23.2

(58) Field of Classification Search
None
See application file for complete search history.

(56) References Cited

FOREIGN PATENT DOCUMENTS

| EP | 0 821 063 | 1/1998 |
| WO | WO 03/072785 | 9/2003 |
| WO | WO 2006/066925 A2 | 6/2006 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
International Search Report for PCT/EP20091008987, filed Jul. 5, 2010.
Foreign-language Written Opinion of the International Searching Authority for PCT/EP2009/008987, filed Jul. 5, 2010.
Jourlin-Castelli, C. et al., "CcpC, a Novel Regulator of the LysR Family Required for Glucose Repression of the citB Gene in *Bacillus subtilis*", Journal of Molecular Biology, vol. 295, No. 4, (Jan. 28, 2000), pp. 865-878.
Hyun-Jin, K. et al., "Regulation of the *Bacillus subtilis* ccpC Gene by ccpA and ccpC", Molecular Microbiology, vol. 43, No. 2, (Jan. 2002), pp. 399-410.
Zhang, F. et al., "Knockout of the HprK Gene in *Bacillus subtilis* CcpA Mutant and Its Influence on Riboflavin Fermentation", Chinese Journal of Biotechnology, vol. 22, No. 4, (Jul. 1, 2006), pp. 534-538.
Yingbo, Z. et al., "Over-Expression of Glucose Dehydrogenase Imrpoved Cell Growith and Riboflavin Production in *Bacillus subtilis*", Biotechnology Letters, vol. 28, No. 20, (Aug. 16, 2006), pp. 1667-1672.
Scanlan E. et al., Database UniProt, "RecName: Full-Uncharacterized HTH-type Transcriptional Regulator ykuM", Database Accession No. 034827, (May 30, 2000), 2 pages.
Chen, X.H. et al., Database UniProt, "SubName: Full=CcpC", Database Accession No. A7Z428, (Oct. 23, 2007), 1 page.
Vitreschak et al, "Regulation of riboflavin biosynthesis and transport genes in bacteria by transcriptional and translational attenuation", Nucleic Acids Research, 2002, vol. 30, No. 14, pp. 3141-3151.

* cited by examiner

*Primary Examiner* — Christian Fronda
(74) *Attorney, Agent, or Firm* — Nixon & Vanderhye P.C.

(57) ABSTRACT

The invention relates to processes and means for the biotechnologically fermentative production of riboflavin (hereinafter also referred to as vitamin B2) and means for the implementation of this process, in particular a modified microbial host cell with increased riboflavin yield. The invention thus provides new processes and means for the regulation of the expression of enzyme activities involved in the riboflavin production of the host cell.

14 Claims, No Drawings

PROCESS FOR THE PRODUCTION OF RIBOFLAVIN

This application is the U.S. national phase of International Application No. PCT/EP2009/008987, filed 15 Dec. 2009, which designated the U.S. and claims priority to DE Application No. 10 2008 063 234.1, filed 15 Dec. 2008, the entire contents of each of which are hereby incorporated by reference.

The invention relates to processes and means for the biotechnologically fermentative production of riboflavin (hereinafter also referred to as vitamin B2) and means for the implementation of this process, in particular a modified microbial host cell with increased riboflavin yield. The invention thus provides new processes and means for the regulation of the expression of enzyme activities involved in the riboflavin production of the host cell.

Riboflavin is a precursor molecule of flavin mononucleotide (FMN) and flavin adenine dinucleotide (FAD). These are essential cofactors for a large number of enzymatic redox reactions in biological cells and organisms. Riboflavin is thus an important additive in the food and animal feed industry. In microorganisms and plants, riboflavin is as a rule synthesized via seven enzymatic reactions from guanosine triphosphate (GTP) from the purine metabolism and ribulose-5-phosphate from the pentose phosphate pathway.

Annually, ca. 4000 tons of riboflavin are produced biotechnologically in various microorganisms. The most important host organisms are bacilli, in particular *Bacillus subtilis*. Apart from these, other microbial cells, including lower eukaryotes, are also used. Examples are the organisms *Eremothecium ashbyii, Ashbya gossypii* and *Candida famata*.

Known biotechnological processes for riboflavin synthesis are in need of improvement, above all with regard to the yield and production rate of riboflavin. There is therefore a need to provide improved production processes and improved host cells, in particular on the basis of the microorganism *Bacillus subtilis*. This relates in particular to the provision of means which enable a particularly simple and effective control of the metabolic activities and in particular enzyme activities which are connected with riboflavin synthesis in the host cell. Further, it relates to the provision of modified host cells with increased riboflavin synthesis particularly in comparison to the wild type.

The inventors have surprisingly found that the transcription factor CcpC has a positive influence on the riboflavin production rate. CcpC belongs to the family of the LysR transcription factors and is known to regulate genes which code for enzyme activities of the tricarboxylic acid cycle (TCA), above all citB and citZ. Surprisingly, it has been found that the riboflavin yield is directly dependent on the activity and/or intracellular concentration of the transcription factor CcpC. Reduced activity of CcpC leads to an increase in the yield. This effect was surprising and not foreseeable from the state of the art, since the enzyme activities in the TCA known to be regulated by CcpC have no direct connection with the metabolic pathways of riboflavin synthesis.

It was also surprising that the biomass production, that is in particular the growth rate of the cells modified according to the invention, in particular CcpC-depleted cells, for example ccpC knockout transformants of *Bacillus subtilis*, remains essentially unchanged.

The present invention thus relates to a modified riboflavin-producing cell or cell line, prokaryotic or eukaryotic cell, in particular a microbial cell, which is characterized in that the activity or concentration of the transcription factor of the CcpC type and/or a homolog or ortholog thereof present and/or expressed in the cell is modified, in particular reduced. Through this modification the cell or cell line is enabled for increased riboflavin production.

In particular, a modified riboflavin-producing microorganism is claimed, wherein the expression and/or the activity of the transcription factor of the CcpC type is reduced, preferably by at least 25%, in comparison to a non-modified or wild type microorganism.

Preferably, the aforesaid cell or cell line is modified such that the gene coding for CcpC is either not expressed at all (suppression of expression) or at least exhibits reduced expression (underexpression), which leads to absent or decreased/reduced activity of the CcpC protein in said cell/cell line. The cell/cell line is preferably a CcpC-depleted mutant or transformant, in particular a knockout mutant of at least one gene coding for CcpC and/or a homolog and/or ortholog thereof.

In this connection, "reduced" is understood to mean both decreased and in particular absent activity of the CcpC protein, or a homolog or ortholog thereof, in its function as a transcription factor, and also decreased and in particular absent expression of the ccpC gene or a homolog or ortholog thereof, which as a result leads to a low copy number or concentration of the gene product CcpC in the cell, in particular a CcpC-depleted cell. Reduced expression is understood to mean a decrease by at least 25%, preferably at least 50, 75, 80, 90, 95, 98 or 100% based on the expression of the ccpC gene in a non-modified (CcpC wild type) cell/cell line. This reduction relates both to the activity of the gene and also the corresponding gene product.

Thus in a cell according to the invention or modified according to the invention, above all the ccpC gene and/or its gene product is suppressed, "knocked-out" or its function (activity) impaired, in particular in comparison to the CcpC wild type, as it is expressed for example in bacilli, preferably in the organism *Bacillus subtilis*.

Various processes for the measurement of the gene or protein activity are known to those skilled in the art. Suitable processes are for example a Northern blot or the use of "gene chip" processes for the measurement of the activity of the ccpC gene and a Western blot by means of specific antibodies against CcpC or a quantitative "2-D SDS-PAGE gel" for the determination of the protein concentration in the cell. The activity of a transcription factor, in particular CcpC, can also be determined indirectly via "gel shift" experiments wherein the quantity of bound CcpC at the corresponding binding sites of the gene to be regulated, such as for example citB or citZ, is measured. By decreasing the gene expression of ccpC the quantity of bound CcpC will also fall, which can be analyzed by quantitative measurement of the signal on the polyacrylamide gel. These and other measurement methods are known to those skilled in the art and can be used for the determination of the activity of CcpC in the sense of the present invention.

Suitable cells or cell lines (summarized as host cells) for the implementation of the present invention are all known riboflavin-producing cells in which the expression of the ccpC gene or homolog or ortholog thereof can be reduced. Examples are prokaryotic or eukaryotic cells, preferably Gram negative or Gram positive bacteria, in particular a microbial cell such as for example *Bacillus, Corynebacterium* or *Pseudomonas*. Preferred are cells of the genus *Bacillus*, e.g. *Bacillus anthracis, Bacillus cereus, Bacillus stearothermophilus, Bacillus halodurans, Bacillus amyloliquifaciens* or *Bacillus subtilis, Bacillus subtilis* being particularly preferred, such as for example *B. subtilis* 168.

A particularly preferred host cell which is suitable for the present invention is *B. subtilis* RB50::[pRF69]$_n$, which comprises multiple copies (e.g. ca. 5 to ca. 20 copies) of the plasmid pRF69, which codes for a modified riboflavin (rib) operon, wherein the modification consists in the insertion of a strong promoter $P_{spo15}$, which results in the intensification of the transcription of the riboflavin genes (see for example EP 405370 and Perkins et al., J. Ind. Microbiol. Biotechnol., 22:8-18, 1999 for the construction of the strain and the culturing conditions for increasing the riboflavin synthesis). *B. subtilis* RB50 and the plasmid pRF69 are respectively deposited in accordance with the provisions of the Budapest Treaty at the "Agricultural Research Culture Collection" (NRRL), Peoria, Ill., USA, Culture Collection Division under the number ("accession number") B 18502 and at the "American Type Culture Collection" (ATCC), P.O. Box 1549, Manassas, Va. 20108 USA under the number ("accession number") ATCC 68338.

In a preferred aspect of the invention, the modification in the ccpC gene is effected in a strain of the genus *Bacillus*, in particular *Bacillus subtilis*. Particularly preferred here is a *Bacillus* strain as host cell, in particular *B. subtilis* strain, deregulated in the riboflavin operon. Examples of a deregulated riboflavin operon are known and include so-called "ribO" and "ribC" mutations. The deregulation causes intensified gene expression of the rib genes. Particularly preferred is a host cell, in particular *Bacillus subtilis*, wherein the gene which codes for the transcription regulator Spo0A is (over)expressed. Thus in a most preferred embodiment, the present invention is implemented in *B. subtilis* RB50 which is mutated to the effect that an active form of the spo0A gene is expressed.

Further microorganisms suitable for the present invention are publicly available via for example the following deposition sites: German Collection of Microorganisms and Cell Cultures (DSMZ), Inhoffenstrasse 7B, D-38124 Brunswick, Germany, "NITE Biological Resource Center", 2-5-8, Kazusakamatari, Kisarazu-shi, Chiba, 292-0818, Japan (previously known as "Institute for Fermentation", Osaka (IFO), 17-85, Juso-honmachi 2-chome, Yodogawa-ku, Osaka 532-8686, Japan) or the "*Bacillus* Genetic Stock Center" (BGSC), The Ohio State University, Columbus, Ohio 43210 USA.

In connection with the present invention, the aforesaid microorganisms also include synonyms and basonyms with the same physiological properties, which are laid down by the "International Code of Nomenclature of Prokaryotes". The nomenclature of the microorganisms in the present invention is that which was officially accepted by the "International Committee on Systematics of Prokaryotes and the Bacteriology and Applied Microbiology Division of the International Union of Microbiological Societies" and was officially published in the "International Journal of Systematic and Evolutionary Microbiology" (IJSEM) at the time of the priority application.

The invention relates to mutated and in particular non-functional genes. The invention relates to mutated and in particular non-functional transcripts therefrom. The invention also relates to mutated and in particular non-functional polypeptides therefrom. Such mutated structures are in the sense of the invention particularly suitable in order to provide genetically modified host cells wherein the function of the CcpC wild type or a homolog or ortholog thereof is reduced or inhibited.

Consequently an essential element of the teaching according to the invention is to reduce the effective, that is active, concentration of the ccpC gene, the CcpC transcript or the translated transcription factor in the cell in order to increase the riboflavin biosynthesis in a host cell. The reduction of the activity and/or the intracellular concentration of CcpC or homologs or orthologs thereof can be achieved in a manner known per se. Those skilled in the art know biotechnological processes and means appropriate for obtaining so-called CcpC-depleted or ccpC knockout mutants or transformants. The invention is therefore not limited to the preferred variants and embodiments described in more detail herein.

According to the invention, the term "mutation" is understood to mean any genetic modification, that is in particular modification at the molecular level, of a nucleic acid molecule which leads to a non-functional "mutated" gene product. In particular it is understood to mean a change in the genome of a microorganism, which interferes with the synthesis of the gene product, that is herein with the synthesis of the transcription factor of the CcpC type and/or leads to the expression of a "mutated" or modified polypeptide, which has a changed "mutated" amino acid sequence and the function whereof has been partly or completely lost in comparison to the CcpC wild type. A mutation according to the invention in the gene or in the gene product leads to changes in at least one step in the expression selected from transcription, translation and if applicable post-translational modification. This mutation is preferably selected from: point mutation, deletion, substitution, insertion and inversion of at least one nucleotide within the gene sequence. The measures for the genetic mutation are however not limited to these preferred embodiments. Those skilled in the art know further possibilities for placing mutations in a gene. The purpose of the mutations according to the invention is the suppression of the expression of at least one gene coding for CcpC. A purpose connected therewith is the expression of a modified transcription factor which compared to the wild type displays a decreased activity, in particular regulatory activity, in the cell.

The "mutation" relates not only to the direct modification of the coding sequence of a gene, but also to the modification of other structures or sequences which are connected with expression. These preferably include structures of the operon of the gene, in particular regulating structures, preferably selected from promoters, regulators, operators, transcription factor binding sites, terminators and cofactors thereof, without wishing to be limited exclusively thereto.

In connection with the invention, "function", particularly in connection with the terms "function-relevant", "function-analogous" and "functioning", is understood to mean the transcription factor function of the CcpC wild type, or a homolog or ortholog thereof for the regulation of the expression of operons or genes, which has an operator structure to which the transcription factor binds. The function of a protein, in particular of a transcription factor such as for example CcpC, is according to the invention also expressed as activity, where the transcription factor function of the CcpC wild type corresponds to a transcription factor activity of 100%. A selection of known suitable methods for the determination of the activity are described above.

A subject matter of the invention is an isolated nucleic acid molecule which represents the ccpC gene, and homologs and orthologs thereof. The invention relates in particular to this gene as represented in the nucleotide sequence SEQ ID No.:1 and as it occurs for example in the organism *Bacillus subtilis*. The invention also relates to the gene product thereof (CcpC protein), represented for example by the amino acid sequence SEQ ID No.:2. The gene ccpC is in particular part of an operon in one of the aforesaid suitable host cells, preferably in *Bacillus subtilis*. Processes for finding homologous/orthologous CcpC sequences are known to those skilled in the art, for example performing a "BLAST" search in a suitable database such as for example EMBL, Genbank, SwissProt, etc. These sequences serve as CcpC wild type, which are then modified according to the present invention, which in an appropriate host organism leads to an increase in the riboflavin biosynthesis. A microorganism which contains this wild type sequence is referred to in connection with the present invention as a wild type microorganism.

The invention thus relates to a—preferably isolated—mutated (modified) nucleic acid molecule, which codes for a "mutated" transcription factor, which is in particular derived from the CcpC type or a homolog or ortholog thereof, where the non-mutated (wild type) nucleic acid molecule is selected from the group consisting of:
a) Nucleic acid molecules which comprise or consist of the nucleotide sequence SEQ ID No.:1;
b) Nucleic acid molecules which code for a polyamino acid molecule (protein) comprising or consisting of the amino acid sequence SEQ ID No.:2;
c) Nucleic acid molecules with a homology to the nucleic acid molecules of a) or b) of at least 70%;
d) Nucleic acid molecules which under stringent conditions hybridize with one of the nucleic acid molecules of a) or b); and
e) Fragments and/or analogs of the nucleic acid molecules according to a) or b), which code for proteins with the function/activity of a transcription factor of the CcpC type, where the mutated nucleic acid molecule exhibits at least one genetic mutation which leads to reduced activity of the CcpC protein in comparison to the activity of the CcpC wild type.

As described above, in a preferred embodiment, the ccpC gene is completely knocked out (so-called knockout mutation).

A further subject matter of the invention is a polyamino acid molecule (protein or polypeptide), preferably a molecule present as isolated, selected from the group consisting of:
a) Polyamino acid molecules which comprise or consist of at least the amino acid sequence SEQ ID No.:2;
b) Polyamino acid molecules which are encoded by a nucleic acid molecule characterized above;
c) Polyamino acid molecules with a homology of at least 70% to the molecules of a) or b); and
d) Fragments and/or analogs of at least one of the polyamino acid molecules of a) or b), which has the function of a transcription factor of the CcpC type,
where the protein of a) to d) is the wild type CcpC, which—as described above—is modified, which results in a reduction of the activity as transcription factor.

The invention also relates to such nucleic acid molecules or proteins which exhibit considerable sequence identity, that is in particular considerable "homology", towards those in the preferred SEQ ID No.:1 or SEQ ID No.:2 respectively. According to the invention, this is understood to mean a homology of at least 70%, preferably at least 75%, particularly preferably at least 80%, at least 85%, at least 90%, at least 95% and at least 98% sequence identity. Preferably the sequence relates to identity to SEQ ID No.:1 or SEQ ID No.:2 respectively over the whole length. In a preferred variant, the aforesaid sequence identity relates exclusively to the function-relevant regions of the sequences SEQ ID No.:1 and SEQ ID No.:2. Examples of such regions are the DNA binding domains in the ccpC gene. Those skilled in the art know programs for identifying these gene regions.

Concerning the "homology" between nucleic acid molecules, hybridization under "stringent conditions" can be understood as one criterion. For "stringent conditions", reference is made to the known technical context as described for example in Maniatis et al., 1989: "Molecular cloning, a laboratory manual", $2^{nd}$ Edition, Cold Spring Harbours Laboratory, N.Y. "Stringent conditions" are dependent on the actual sequence. As a rule, this is understood to mean a hybridization temperature which is 5 to 10 K lower than the melting point of a specific sequence, at which 50% sequence-identical complementary probes hybridize to the target sequence. Conditions under which nucleic acid sequences of at least 50%, 60, 70% or particularly preferably of at least 80%, most preferably of at least 85% to 90%, in particular of at least 95% are homologous to one another are preferred.

In an embodiment of a hybridization under stringent conditions given as an example the reaction is performed in 6× sodium chloride/sodium citrate (SSC) at ca. 45° C. with subsequent washing in 1×SSC, 0.1% SDS at 50° C., preferably 55° C., particularly preferably 60° C., especially preferably at 65° C.

Preferred is a hybridization under "highly stringent conditions", such as for example an incubation at 42° C. for several days, for example 2 to 4 days, with the use of a labeled probe, such as for example a probe labeled with digoxygenin (DIG), followed by one or more washing steps in 2×SSC, 0.1% SDS at room temperature and at least 1 washing step in 0.5×SSC, 0.1% SDS or in 0.1×SSC, 0.1% SDS at 65 to 68° C. In particular "highly stringent conditions" for example comprise an incubation for 2 hours to 4 days at 42° C. with the use of a DIG-labeled probe (prepared for example by means of the "DIG labeling system", Roche Diagnostics GmbH, 68298 Mannheim, Germany) in a solution such as for example "DigEasyHyb solution" (Roche Diagnostics GmbH) and the optional addition of 100 μg/ml salmon sperm nucleic acid, or in a solution containing 50% formamide, 5×SSC, 0.02% SDS, 0.1% N-laurylsarcosine and 2% "blocking reagent" (Roche Diagnostics GmbH), followed by washing twice for 5 to 15 minutes in 2×SSC, 0.1% SDS at room temperature and washing twice for 15 to 30 minutes in 0.5×SSC, 0.1% SDS or in 0.1×SSC, 0.1% SDS at 65 to 68° C.

In the present application, the terms "homology" or "percentage identity" are used interchangeably. In order to determine the percentage to which two nucleic acid or amino acid sequences are "homologous" or "identical" to one another, both sequences are adjusted for the optimal comparison (thus for example gaps are introduced into one sequence for the optimal alignment of the two sequences). The nucleotides at corresponding positions are then compared. If a position in the first nucleic acid sequence is occupied by the same nucleotide at the corresponding position in the second sequence, both molecules are identical at this position, which corresponds to a homology or identity of 100%. The percentage value of the identity (percentage identity) between two sequences can be represented as a function of a large number of identical positions which both sequences have in common [i.e. % identity=number of identical positions/total number of positions (i.e. overlapping positions)×100]. The sequences to be compared preferably have the same length. For the determination of the homology various known computer programs are available to those skilled in the art, for example the program "GAP" as a component of the GCG software package (available at http://accelrys.com/) which operates according to the algorithm of Needleman and Wunsch (J. Mol. Biol. 48, 444-453, 1970).

In connection with the present invention, the term "orthologs" should be understood to mean genes of different genera which have all arisen starting from one common original gene. Normally, the function of these orthologous genes is conserved during evolution. The identification of orthologs is important in order to be able to make a reliable prediction of gene function in previously unsequenced genomes.

In contrast to this, in the sense of this invention genes which indeed derive from one common gene, but in the course of evolution have acquired another function, are referred to as "analogs".

In a preferred embodiment, the invention provides the modification, in particular reducing the activity, of the binding affinity of the transcription factor CcpC, or a homolog or ortholog thereof, and/or the interaction thereof with an operon of the regulated gene, in particular the transcription factor binding structure, and/or of a cofactor thereof, such that modified or "mutated" gene products derived from CcpC, or homologs or orthologs thereof, i.e. proteins, are obtained showing decreased or no binding activity and/or interaction with the operator structures which are connected with the regulated gene or operon.

In a preferred variant, this is carried out by direct genetic modification of the original ccpC gene (wild type) or homologs or orthologs thereof, so that a gene product with a modified "mutated" amino acid sequence is obtained, in particular with a modified protein structure.

In an alternative or preferably additional variant, this is carried out by modifying at least one process, selected from transcription, translation and if applicable post-translational processing, particularly preferred modification of at least one molecular structure connected with these processes or of a cofactor for these. This is in particular effected by use of at least one structure or of a construct, which binds and/or inactivates the structure or sequence involved in at least one of these processes. This structure or the construct is preferably selected from antisense constructs and antibodies, without being exclusively limited thereto.

Preferably, the activity and/or concentration of the transcription factor CcpC, or homologs or orthologs thereof, is directly reduced by means of specific inhibitors. Examples of such specific inhibitors are antisense constructs of the CcpC gene, or homologs or orthologs thereof, or of other structurally related nucleic acid molecules according to the invention, which are transiently or stably introduced into the host cell in a manner known per se and which are expressed therein.

In another preferred embodiment, the invention provides the modification, in particular reduction of concentration/activity, i.e. in particular the copy number, of expression of the transcription factor CcpC and its homologs or orthologs, respectively, and/or if necessary the expression of a Co-factor thereof, in particular to reduce or completely suppress said expression. In a preferred variant, this is effected by direct genetic modification of the operon of the ccpC gene or homologs or orthologs thereof. In a preferred variant, the modification of the promoter controlling the expression of the gene is provided for this, and preferably such that underexpression occurs or the expression does not occur at all, in other words is "knocked out".

In an alternative or preferably additional variant, this is effected by modulating at least one process, selected from transcription, translation and if applicable post-translational processing, preferably in particular of at least one molecular structure connected with these processes or of a cofactor for these. These include in particular knockout mutations, which can for example be obtained by means of homologous recombination, and also the use of antisense constructs in a manner known per se.

The nucleic acids or antisense constructs according to the invention can be introduced into the host cell by generally known methods. Preferred methods are the disintegration of the cell wall and/or membrane of the host cell preferably by electroporation, detergents or analogous means and alternatively or preferably in addition by ballistic processes (e.g. "gene gun") or analogous processes, without the invention being limited to these processes and means.

Hence one aspect of the invention is an externally and in particular synthetically produced DNA or RNA molecule with a nucleotide sequence according to the invention in antisense orientation, which can be introduced into the host cell. This in particular includes vectors which comprise one or more copies of this nucleic acid molecule in antisense orientation.

Accordingly, a preferred embodiment of the invention is a modified microbial cell which is modified for suppression of the expression of CcpC, or homologs or orthologs thereof. In one variant, the cell is modified for underexpression of CcpC, or homologs or orthologs thereof. In a preferred embodiment, the cell is a knockout mutant of at least one gene which codes for CcpC. The invention thus also includes modified cells which are knockout mutants of homologs of the CcpC coding gene of *Bacillus subtilis*. The invention thus also includes knockout mutants of orthologs of the CcpC coding gene of *Bacillus subtilis*. The invention also includes knockout mutants of other function-analogs of CcpC and the gene(s) thereof.

In an alternative or preferably additional variant of the genetic modification of the host cell, the genetic modification takes place at least one and preferably several binding structures and fragments thereof of the CcpC transcription factor. These are preferably the operator structures of the genes regulated by CcpC in the host cell. Regulated genes are in particular citB and citZ, without the invention being intended to be limited thereto. Through the at least one preferably provided mutation according to the invention near the operator segment of the gene regulated by CcpC, according to the invention the binding of the transcription factor to the operator should be prevented or decreased, so that the regulating effect with regard to the transcription of the gene occurs to a reduced extent or not at all. Processes for the modification of the operator segments of the genes regulated by transcription factors and in particular their binding sequences for transcription factors are known to those skilled in the art. Binding sequences of the regulated genes citB and citZ and in the ccpC gene itself are for example published/referenced in the "database of transcriptional regulation in *Bacillus subtilis*" (DBTBS; see http://dbtbs.hgc.jp/). Examples of known binding sequences in regulatory sequences of the ccpC gene itself are located at position −10 to +15 (SEQ ID No.:3), in particular position −5 to +10 (SEQ ID No.:8), relative to the start codon. Known binding sequences of citB are located at position −75 to −52 (SEQ ID No.:4), in particular position −73 to −68 (SEQ ID No.:9) or position −64 to −60 (SEQ ID No.:10), and at position −35 to −22 (SEQ ID No.:5) or position −35 to −17 (SEQ ID No.:11), in particular position −27 to −22 (SEQ ID No.:12), relative to the start codon, and known binding sequences of citZ are located at position −11 to +5 (SEQ ID No.:6), in particular position −11 to −8 (SEQ ID No.:13), and at position +21 to +44 (SEQ ID No.:7), in particular position +23 to +26 (SEQ ID No.:14) or position +34 to +37 (SEQ ID No.:15), relative to the start codon. The aforesaid known binding sequences and the corresponding operons are listed in table 1.

TABLE 1

List of known genes and their operons which are regulated by CcpC.

| Operon | Regulated gene | Absolute position | Position relative to start codon | Binding sequence (cis element) |
|---|---|---|---|---|
| ykuJK-ykzF-ykuL-ccpC | ccpC | 1485309 ... 1485333 | −10:+15 | GGGAGATAAGAAAAACT TATTGATA (SEQ ID No.: 3) |
| citB | citB | 1925746 ... 1925769 | −75:−52 | TCATAAGTCGAACTTATT GTATTT (SEQ ID No.: 4) |
| citB | citB | 1925781 ... 1925799 | −35:−22 | TGATATTTACTTATGTATG (SEQ ID No.: 5) |
| citZ-icd-mdh | citZ | 2981498 ... 2981513 | −11:+5 | ATAATGAGAATAGGCT (SEQ ID No.: 6) |
| citZ-icd-mdh | citZ | 2981459 ... 2981482 | +21:+44 | TTATAAAAATTTGTTAT GTTCTTT (SEQ ID No.: 7) |

The "absolute position" was calculated on the basis of the position in the "NCBI sequence file (accession no. NC 000964)".
The exact binding sequence (cis element) is underlined.
Source: http://dbtbs.hgc.jp/.

The present invention thus relates to a modified host cell which contains a modification/mutation in the ccpC gene which leads to reduced expression of the gene (see above). However in a further embodiment the host cell can also be modified such that it comprises a modification/mutation in a binding sequence for the ccpC gene product, preferably in one of the binding sequences described above according to SEQ ID No.:3, 4, 5, 6, 7, 8, 9, 10, 11, 12, 13, 14 or 15, whereby the binding of CcpC is reduced. This reduced binding should be understood as reduced activity of CcpC, as described above, a reduced activity of at least 25% in comparison to the activity of the wild type being preferred, which corresponds to binding reduced by at least 25%. The invention also relates to the use of transcripts thereof and the proteins synthesizable therefrom and antisense constructs thereof for regulating, in particular increasing, the riboflavin synthesis in host cells in the sense of the teaching described herein. Processes for the introduction of mutations and subsequent measurement of the binding activity, such as for example the implementation of a "gel-shift" experiment or of a "footprint" experiment (see e.g. Maniatis et al., 1989: "Molecular cloning, a laboratory manual", 2$^{nd}$ Edition, Cold Spring Harbours Laboratory, N.Y.), are known to those skilled in the art.

The invention also relates to molecules binding to the aforesaid molecules and structures. Such molecules are suitable according to the invention for modifying, in particular suppressing, the function or activity of CcpC, or the homologs or orthologs. Preferably such molecules bind to at least one of the structures or molecules definable by the nucleotide sequences, selected from SEQ ID No.:1, 3, 4, 5, 6, 7, 8, 9, 10, 11, 12, 13, 14, and SEQ ID No.:15, in particular operator structures. Preferably, the binding molecules are specific antibodies against the structures thus definable.

Accordingly a subject matter of the invention is a, monoclonal or polyclonal, antibody, which can bind specifically to one according to the aforesaid polyamino acid sequences or molecules. Through binding of the antibody to CcpC, binding of the transcription factor to the operator sequences in the genes to be regulated, such as for example citB or citZ, is prevented.

The modified nucleic acid molecules and modified host cells described above are used for increasing riboflavin synthesis. The present invention thus also relates to a process for the biotechnological synthesis of riboflavin, which in particular includes the following steps:
a) Provision of a modified host cell according to the present invention,
b) Culturing of the modified host cell in a suitable culture medium and under suitable culture conditions which enable the synthesis of riboflavin in the host cell, and optionally
c) Isolation of the riboflavin from the modified host cell and/or the culture medium.

A particular aspect of the invention is the fermentative production of riboflavin by means of the aforesaid modified host cells. According to the present invention, the term "riboflavin" includes both riboflavin, and also flavin mononucleotide (FMN) and flavin adenine dinucleotide (FAD) and precursor molecules thereof ("precursors"), derivatives and/or salts of riboflavin, FMN or FAD. Examples of salts are in particular riboflavin-5-phosphate and sodium riboflavin-5-phosphate. Precursor molecules and derivatives of riboflavin, FMN or FAD include for example DRAPP, 5-amino-6-ribosylamino-2,4(1H,3H)-pyrimidinedione-5'-phosphate, 2,5-diamino-6-ribitylamino-4 (3H)-pyrimidinone-5'-phosphate, 5-amino-6-ribitylamino-2,4(1H,3H)-pyrimidinedione-5'-phosphate, 5-amino-6-ribitylamino-2,4(1H,3H)-pyrimidinedione, 6,7-dimethyl-8-ribityllumazine (DMRL) and flavoproteins.

General processes for the fermentative synthesis of riboflavin and the genes involved in riboflavin biosynthesis, in particular the fermentative synthesis in Bacillus, are known (see e.g. EP 405370 or "Ullman's Encyclopedia of Industrial Chemistry", 7$^{th}$ Edition, 2007, Chapter: Vitamins). These processes can also be applied to riboflavin synthesis by means of the modified host cells described herein.

Various substrates can be used as the carbon source in the process according to the invention for riboflavin synthesis. Particularly suitable carbon sources can be selected from compounds with 3, 5 or 6 carbon atoms, for example, D-glucose, glycerin, "thick juice", dextrose, starch, saccharose or ribose. Preferably the carbon source is D-glucose. The terms "carbon source", "substrate" and "production substrate" in connection with the process described herein are used mutually interchangeably.

As the (culture) medium for the process according to the invention for riboflavin synthesis by means of modified host cells all media suitable for riboflavin synthesis can be used. This is typically an aqueous medium which contains for example salts and substrate(s) and has a specific pH. The medium in which the substrate is converted into riboflavin is also referred to as the production medium.

"Fermentation" or "production" or "fermentation process" in connection with the present invention refers to both the use of growing cells in a medium under conditions which are known to those skilled in the art, and also the use of no longer growing cells (so-called "resting cells"), after these have grown in the appropriate medium under the conditions known to those skilled in the art. These growing or no longer growing cells are used for the conversion of a suitable substrate into riboflavin, under conditions which are known to those skilled in the art.

The synthesized riboflavin can be obtained/isolated from the host cells by suitable methods. This can for example mean the separation of the riboflavin from the production medium. Optionally, the riboflavin obtained can then be further processed, for example purified.

In connection with the above process for the production of riboflavin by means of modified host cells the growth phase of the microorganisms normally takes place under aerobic conditions in an aqueous medium with addition of appropriate nutrients. The culturing can for example take place in a batch, fed-batch, semi-continuous or continuous process, fed-batch or semi-continuous being preferred.

Depending on the host cells, the pH, the temperature and the nutrient medium, the duration of the culturing is for example ca. 10 hours to ca. 10 days, preferably ca. 4 to ca. 7 days, particularly preferably ca. 2 to ca. 6 days. Those skilled in the art know the optimal conditions for the selected host cell.

The culturing is for example performed at a pH of ca. 7.0, preferably between ea. 6 to ca. 8, particularly preferably between ca. 6.5 to 7.5 and a suitable temperature from ca. 13° C. to ca. 70° C., preferably from ca. 35° C. to ca. 39° C., particularly preferably from ca. 30° C. to ca. 39° C., in particular from ca. 36° C. to ca. 39° C. The culture medium normally comprises D-glucose, glycerin, "thick juice", dextrose, starch, saccharose or ribose as the carbon source, nitrogen sources, such as for example peptone, yeast extract or amino acids. In addition, salts can be present, for example magnesium sulfate, manganese sulfate, calcium phosphate or calcium carbonate. An example of fermentative production of riboflavin by means of cells of Bacillus subtilis is described in WO 04/113510 (VF medium), which is incorporated herein as a reference. This method should preferably be used for the present invention.

Through the modification in the activity of the transcription factor CcpC, as described above, the (modified) host cell is capable of increased riboflavin synthesis. The riboflavin yield of a host cell according to the invention, in particular of the strain Bacillus subtilis, can be increased by at least 10%, compared with the yield of riboflavin of a non-modified or wild type cell. Increases by at least 20%, in particular at least 30%, 40%, 50%, 60%, 80% and more, are preferred. Analytical methods for the determination of the yield/productivity of riboflavin are known. Examples are HPLC or the use of indicator strains (see for example Bretzel et al., J. Ind. Microbiol. Biotechnol. 22, 19-26, 1999). After fermentation has taken place, the riboflavin produced is separated from the other components (culture medium, biomass, etc.), purified and the concentration determined by the known methods, a control reaction being performed with a wild type strain.

Terms such as "production" or "preparation" and "productivity" are known to those skilled in the art and include the concentration of riboflavin, which is formed in a given time and a given fermentation volume (e.g. kg product per hour per liter). The term "yield" is known to those skilled in the art and comprises the efficacy of the conversion of the carbon source into the product, i.e. riboflavin. The yield is generally expressed as kg of product per kg of carbon source. In connection with the present invention, an "increase in the yield and/or the productivity" means an increase in the quantity of molecules obtained in a given culture volume in a given time period.

EXAMPLES

All media used but not listed are described in WO2007/051552.

100× trace element solution A: 12.5 g $MgCl_2.6H_2O$; 0.55 g $CaCl_2$; 1.35 g $FeCl_2.6H_2O$; 0.1 g $MnCl_2.4H_2O$; 0.17 g/l $ZnCl_2$; 0.043 g $CuCl_2.2H_2O$; 0.06 g $CoCl_2.6H_2O$; 0.06 g $Na_2MoO_4.2H_2O$; made up to 1 l $H_2O$, autoclaved.

5× minimal salt solution: 0.057 M $K_2SO_4$; 0.31 M $K_2HPO_4.5H_2O$; 0.22 M $KH_2PO4$; 0.017 M Na citrate.$7H_2O$; 0.004 M $MgSO_4H_2O$, pH 7.0, autoclaved.

100× trace element solution B: 0.55 g $CaCl_2$; 0.17 g $ZnCl_2$; 0.043 g $CuCl_2.2H_2O$; 0.06 $CoCl_2.6H_2O$; 0.06 g $Na_2MoO_4.2H_2O$; made up to 1 l $H_2O$, autoclaved.

Riboflavin screening medium (RSM): 200 ml 10× Spizien salts; 10 ml 100× trace element solution A; 2 ml 50% glucose; 36 ml 25% raffinose; 10 ml 10% yeast extract; made up to 1 l $H_2O$.

Spizien minimal medium (SMM): 100 ml 10× Spizien salts; 10 ml 50% glucose; 1 ml 40% sodium glutamate; 10 ml trace element solution A; made up to 1 l $H_2O$.

Riboflavin production in shaker flasks was tested as follows: 5 ml VY medium were inoculated starting from a frozen glycerin stock and cultured for 6-8 hrs at 37 C with shaking (280 rpm). The 5 ml cultures were used directly for the inoculation of 25 ml RSM medium in 250 ml flasks. After incubation for 48 hrs at 39 C with shaking (220 rpm), 500 µl of culture liquid were treated with 35 ml 4 N NaOH and shaken vigorously for one minute. The samples were treated with 465 ml potassium phosphate buffer (pH 6.8) and centrifuged for 5 mins at 13200 rpm. The riboflavin, 6,7-dimethyl-8-ribityllumazin (DMRL) and oxolumazine content was determined by HPLC. A second culture sample was centrifuged (5 min, 13200 rpm) and the supernatant was used for the determination of residual glucose and raffinose. The determination of the values enabled the calculation of the yield.

Shaker culture samples were analyzed by HPLC. The chromatography was performed on an Agilent 1100 HPLC system, which was equipped with an equilibrated autosampler, a diode array and a fluorescence detector. The separation was effected on a Supelcosil LC-8DB 5µ column (150 mm×4.6 mm), which was equipped with a 4 mm LC-8DB guard column. A mixture of 0.1 M acetic acid and methanol was used as the mobile phase. The elution was performed by means of gradients. After 5 mins at a concentration of 2% methanol, the methanol concentration was increased to 50% in 15 mins. The column was equilibrated at 20 C. A UV signal at 280 nm was used for the detection. Riboflavin was detected as an isolated peak after 15.2 mins. The calibration of the method was performed with riboflavin from Fluka and was linear from 10 mg/l to 1 g/l. For the determination of glucose and raffinose from the culture broth, an Agilent 1100 HPLC system, to which a quaternary pump, an autosampler, and refractive index detector were attached, was also used. The separation was achieved on a CAPCELL PAK NH2 UG80 column (4.6 mm×250 mm, 5µ) from Shiseido. The optimal column temperature was 35 C. The mobile phase was a mixture of acetonitrile and deionized water in a ratio of 65/35. The flow rate was set at 1 ml/min. The injection volume was 5 µl. The refractive index detector signal was used for the detection. The method could be used for concentrations from 0.5 g/l to 30 g/l.

Example 1

Simulation of the Riboflavin Yield with Change of Activity of CcpC

In order to predict the metabolic flux distribution in the riboflavin synthesis in a host cell with an activity change according to the invention, in particular a decrease in the activity, of the transcription factor CcpC, in a first step changes in the activity of CcpC are identified and their influence on the genes regulated by CcpC quantified with "Network Component Analysis" (NCA) and gene expression time series. For prediction of the influence of the transcription factor activity, regulated fluxes of the starting flux distribution are diverted and then a new metabolic flow distribution is calculated via quadratic convex optimization. The simulation was performed taking the riboflavin-producing *Bacillus subtilis* strain during aerobic growth on glucose as the example.

A mutant with a CcpC activity less than 1 (AF<1, e.g. knockout mutant) exhibits a markedly increased riboflavin yield compared to the wild type (AF=1), namely a yield of 0.05 in comparison to 0.02 (g riboflavin per g glucose).

Example 2

Generation of a CcpC-Deficient Strain

For the preparation of a knockout mutant for the transcription factor CcpC in the host cell *Bacillus subtilis* an antibiotic resistance gene cassette was introduced at the original ccpC locus of the genome of *B. subtilis*.

Two DNA fragments which had been amplified by means of PCR from the genomic DNA of *B. subtilis* 168 were combined with a neomycin resistance gene cassette in a third PCR (Itaya et al., 1989, A neomycin resistance gene cassette selectable in a single copy state in the *Bacillus subtilis* chromosome, Nucleic Acids Res. 17: 4410). For the preparation of the two fragments, which were homologous to the 5' and to the 3' regions of the gene ccpC, the following PCRs were performed: 5'-homology fragment, 100 ng genomic DNA from *B. subtilis* 168, 1 µl of a 100 µM solution of primer p436 (SEQ ID No.:16), 1 µl of a 100 µM solution of primer p439 (SEQ ID No.:17), 1 µl of a 10 mM dNTP solution, 5 µl 10× buffer, and 0.5 µl Pfu polymerase (Stratagene) in 50 µl. The PCR reaction consisted of 35 cycles: (i) denaturation at 94° C. for 30 sec; (ii) annealing at 52° C. for 30 see; (iii) amplification at 72° C. for 1 min. Before the actual PCR reaction, the template DNA was denatured for 3 mins at 95° C. In the case of the 3' DNA fragment, the primer pair primer p437 (SEQ ID No.:18) and primer p438 (SEQ ID No.:19) was used. The DNA fragment which coded for neomycin resistance gene cassette was prepared under the same conditions with the primer pair p9 (SEQ ID No.:20) and p10 (SEQ ID No.:21). In a fourth PCR, the three DNA fragments were now bound together via their homologous, overlapping regions. For this, 50 ng of each of the DNA fragments purified by an agarose gel electrophoresis were used. Compared to the PCR conditions stated above, the amplification time was increased to 2.5 mins. All other parameters remained unchanged. As the primer pair, primers p45 and p51 were used. The resulting PCR product was purified by means of the QiaQuick PCR purification kit from Qiagen. Competent *B. subtilis* 168 cells were transformed with 2 µg of purified product. Selection for neomycin-resistant colonies was performed on TBAB medium which contained 2 mg/l neomycin. By means of a further PCR (primer pair p45 and p10 under the aforesaid conditions) the genotype of selected neomycin-resistant transformants was confirmed. One positive transformant was given the designation BS5878.

Example 3

Transfer of the ccpC Knockout into Selected Riboflavin-Overproducing Strains

For the transfer of the ccpC knockout into selected *B. subtilis* strains which overproduce riboflavin, transduction with the phage PBS-1 was used (see WO 07/051552, Example 6). A PBS-1 phage lysate of the strain BS5878 was prepared. The riboflavin producers BS3914 and BS3917 used for the transduction were prepared as follows: strain BS3914 and BS3917 are descendants of the riboflavin-overproducing strain BS3534 (for the construction of BS3534 see WO 2007/051552). BS3534 is based on the strain *B. subtilis* RB50, which was described in the patent EP 405370 and was deposited under the number NRRL B-18502. In the strains BS3914 and BS3917, the plasmid pRF69 integrated in the riboflavin locus was replaced by a neomycin resistance gene cassette. For the preparation of the corresponding PCR product, the PCR method described above was used. The PCR product consisted of a 526 bp long 3' region upstream from the riboflavin operon promoter (primer pair p50; SEQ ID No.:22 and p51; SEQ ID No.:23) on the genomic DNA of *B. subtilis* 168 and a 502 bp long 5' region in the ribD gene (primer pair p44; SEQ ID No.:24 and p45; SEQ ID No.:25) on the genomic DNA of *B. subtilis* 168 which were fused with the neomycin resistance gene cassette (primer p9 and p10 on the plasmid pUB110) by means of PCR. The exact reaction conditions are described further above. The purified PCR product was used for the transformation of competent *B. subtilis* 168 cells. The selection took place on TBAB plates which contained 100 mg/l riboflavin and 2 mg/l neomycin. The genotype of grown colonies was confirmed by means of PCR and sequencing. One confirmed, isolated transformant was designated as BS3813. A PBS-1 phage lysate of BS3813 was prepared for the transfer of the construct into strain BS3534. The strain thus prepared was given the designation BS3798.

In the next step, the neomycin resistance cassette of the riboflavin-auxotrophic strain BS3813 was again replaced by a functional riboflavin operon. For the selection of positive transformants/transductants, minimal medium plates (2 g/l glucose dissolved in the 1× mineral salt solution—trace element solution) were used. In the modified promoter/mRNA leader sequence, the native promoter was replaced with the promoter of the veg gene of *B. subtilis*. In addition, a cytosine in the leader region was replaced with a thymidine (SEQ ID No.:26). Competent cells of the strain BS3813 were transformed with a DNA fragment which possessed the sequence according to SEQ ID No.:26. Transformed cells again possessed the ability to grow in a medium without addition of riboflavin. The genotype of grown colonies was confirmed by PCR and subsequent sequencing. One confirmed colony was designated as BS3953. A PBS-1 phage lysate of the strain BS3953 was used for the transduction of BS3798. The selection was performed as described above. Two types of transductants were isolated. In the first case, the inactivated spo0A gene of BS3798 had not been replaced with the wild type allele. One confirmed transductant received the designation BS3914. In the second case, the inactivated spo0A gene had been replaced with the active wild type form owing to the transfer of a larger piece of DNA during the transduction. One tested, Spo0A-positive mutant was named BS3917.

BS3914 and BS3917 were now transducted with the lysate from BS5878. Once again, the selection took place on TBAB plates which contained 2 mg/l neomycin. The genotype of selected transductants was confirmed with the aforesaid PCR. Five confirmed transductants from the transduction of the strain BS3914 were given the designations BS5891, BS5893, BS5894 and BS5895. Four transductants which were derived from BS3917 received the designation BS5887 to BS5890.

The riboflavin production of the newly generated strains was tested as described above in the shaker flask. After 48 hrs, a sample of 500 µl was taken from the cultures, treated with 4 N NaOH, neutralized and the riboflavin concentration of the sample determined by HPLC after centrifugation. For the calculation of the yield, the sugar concentration in the final sample was also determined. The results are summarized in table 2A and 2B.

TABLE 2A

Riboflavin yield in the shaker flask test of the newly prepared ccpC knockout strains based on BS3914. The riboflavin yields of the new strains were compared with the riboflavin yield of the host strain BS3914.

| Strain | Riboflavin yield [%] | Increase [%] |
|---|---|---|
| BS3914 | 4.67 | 100 |
| BS5891 | 4.77 | 102 |
| BS5893 | 4.78 | 102 |
| BS5894 | 4.66 | 100 |
| BS5895 | 4.76 | 102 |

TABLE 2B

Riboflavin yield in the shaker flask test of the newly prepared ccpC knockout strains based on BS3917. The riboflavin yields of the new strains were compared with the riboflavin yield of the host strain BS3917.

| Strain | Riboflavin yield [%] | Increase [%] |
|---|---|---|
| BS3917 | 5.91 | 100 |
| BS5887 | 7.32 | 122 |
| BS5888 | 6.95 | 118 |
| BS5890 | 6.90 | 117 |

Transductants which are derived from the strain (BS3914) produced riboflavin with the same yield as the host strain BS3914. The ccpC knockout strains of the Spo0A-plus strain BS3917 produced riboflavin with a yield markedly improved over the host strain BS3917. Even BS3917 itself exhibited a significantly better yield (25%) than the Spo0A-minus strain BS3914 under the stated conditions.

It can thus be concluded that the inactivation of ccpC in a riboflavin-producing B. subtilis strain which possesses an active spo0A gene effects an improvement in the yield of at least 20% under shaker flask conditions.

With a partial inactivation of ccpC, i.e. the introduction of mutations into the gene sequence which lead to a diminution of the transcription function, for example to a diminution of the activity by 75%, 50% or 25%, and subsequent determination of the riboflavin concentration, an increase by ca. 10 to a maximum of 20% in comparison to the wild type strain can be observed. These results can also be achieved by insertion of mutations into the binding sequences for CcpC (see table 1) whereby, depending on the diminution in the binding affinity, increases in the riboflavin concentration in the region of ca. 25% can be achieved. The mutations described above are inserted according to a standard protocol, and thereafter the binding affinity or the reduction in the binding affinity can be determined by means of known methods (see Description) and the quantity of riboflavin determined as described above.

The invention claimed is:

1. A process for the production of riboflavin, comprising culturing a riboflavin-producing microorganism of the genus *Bacillus* such that riboflavin is produced, said microorganism comprising a CcpC transcription factor with an expression and/or activity reduced by at least 25% in comparison to a respective non-modified or wild type microorganism wherein said expression and/or the activity of the transcription factor of the CcpC type is not reduced, wherein the amount of riboflavin is increased by at least 10% compared to a respective non-modified or wild type microorganism.

2. The process as claimed in claim 1, wherein the CcpC transcription factor comprises a mutation in one or more cis-acting binding sequences for CcpC.

3. The process of claim 2, wherein the mutation within the nucleotide sequence of ccpC is in a sequence according to SEQ ID NO.: 3 or fragments thereof.

4. The process of claim 1, wherein the gene coding for CcpC is knocked out in said microorganism.

5. The process of claim 1 wherein the Ccpc transcriptional factor to be modified is encoded by a gene comprising a nucleic acid molecule selected from the group consisting of:
   a) a nucleic acid molecule which comprise the nucleotide sequence SEQ ID NO.:1;
   b) a nucleic acid molecule which codes for a polyamino acid molecule (protein) comprising the amino acid sequence SEQ ID NO.:2;
   c) a nucleic acid molecule with homology to the nucleic acid molecule of a) or b) of at least 80%;
   d) a nucleic acid molecule which under highly stringent conditions hybridizes with one of the nucleic acid molecules of a) or b), said highly stringent conditions comprising hybridization at 42° C. for 2 to 4 days followed by two washes in 2×SSC, 0.1% SDS at room temperature for 5 to 15 min and two washes in 0.5×SSC, 0.1% SDS or 0.1×SSC, 0.1% SDS at 65 to 68° C. for 15 to 30 min; and
   e) a fragment and/or analog of the nucleic acid molecules according to a) or b), which comprises a cis-acting binding sequence for a protein encoded by a nucleic acid molecule according to a) or b).

6. The process of claim 1, further comprising the steps of:
   a) Culturing the microorganism under fermentation conditions suitable for riboflavin production, and
   b) Isolation of the riboflavin from the culture medium and/or the modified host cell.

7. The process of claim 3 wherein the microorganism comprises a mutation in a sequence according to SEQ ID NO: 8.

8. The process of claim 1 wherein the microorganism is selected from the group consisting of *Bacillus amyloliquifaciens* and *Bacillus subtilis*.

9. The process of claim 2 wherein the microorganism is selected from the group consisting of *Bacillus amyloliquifaciens* and *Bacillus subtilis*.

10. The process of claim 3 wherein the microorganism is selected from the group consisting of *Bacillus amyloliquifaciens* and *Bacillus subtilis*.

11. The process of claim 4 wherein the microorganism is selected from the group consisting of *Bacillus amyloliquifaciens* and *Bacillus subtilis*.

12. The process of claim 5 wherein the microorganism is selected from the group consisting of *Bacillus amyloliquifaciens* and *Bacillus subtilis*.

13. The process of claim 6 wherein the microorganism is selected from the group consisting of *Bacillus amyloliquifaciens* and *Bacillus subtilis*.

14. The process of claim 7 wherein the microorganism is selected from the group consisting of *Bacillus amyloliquifaciens* and *Bacillus subtilis*.

* * * * *

SEQUENCE LISTING

<160> NUMBER OF SEQ ID NOS: 26

<210> SEQ ID NO 1
<211> LENGTH: 882
<212> TYPE: DNA
<213> ORGANISM: Bacillus subtilis

<400> SEQUENCE: 1

```
atgcagcttc aagagcttca tatgctcgta gttttagctg aggaattaaa tatgagaaag      60
gcggcagaac ggcttttgt atctcagccg gctttatctc agcgcttaca aaccattgaa     120
aaggcgtggg gaacaaaaat ctttttaaga tctcaaaaag gattaacggt aacgcccgcc     180
ggtgagaaaa tcattcagtt tgcgaatgat gtgacattag agcaggaaag aataagagaa     240
aatattgacg agcttgaagg tgaaattcac ggcacattga agcttgccgt cgcctccata     300
atcggtcagc attggctccc taaagtcctg aagacgtatg tggaaaagta tccgaatgca     360
aagatctcgc tcataaccgg gtggagcagc gaaatgctga aaagcttgta tgaggatcag     420
gttcatatcg gcattataag aggcaaccct gagtggaagg ggcgcaaaga ttacttaatg     480
acagatcatc tgtatttagt ggatactgaa atttcctgca tcgaagatat tgcccataca     540
```

```
gaacgtccgt ttatccagtt taaaagtgac agcacttatt ttcaggaaat tcagcactgg    600
tggcatcaaa aatttaaaac gtcgccgaaa cagacgatat tggttgatca gattgaaacg    660
tgcaaacaga tggcgctgca cggaatcggt tatgccattt tgccgtctgt taccctcaa    720 aatgaagata aagtgaataa aatgcctctt ttagacatga aagggcatcc gatcggtcgg    780
gatacatggt tattaggtta tgagcctgcc tttgaactga aacaagttca agcttttgta    840
caagtgataa aggatatgct ggatcaggaa aatccatttt aa                      882

<210> SEQ ID NO 2
<211> LENGTH: 293
<212> TYPE: PRT
<213> ORGANISM: Bacillus subtilis

<400> SEQUENCE: 2

Met Gln Leu Gln Glu Leu His Met Leu Val Leu Ala Glu Glu Leu
1               5                   10                  15

Asn Met Arg Lys Ala Ala Glu Arg Leu Phe Val Ser Gln Pro Ala Leu
            20                  25                  30

Ser Gln Arg Leu Gln Thr Ile Glu Lys Ala Trp Gly Thr Lys Ile Phe
        35                  40                  45

Leu Arg Ser Gln Lys Gly Leu Thr Val Thr Pro Ala Gly Glu Lys Ile
50                  55                  60

Ile Gln Phe Ala Asn Asp Val Thr Leu Glu Gln Gly Arg Ile Arg Glu
65                  70                  75                  80

Asn Ile Asp Glu Leu Glu Gly Glu Ile His Gly Thr Leu Lys Leu Ala
                85                  90                  95

Val Ala Ser Ile Ile Gly Gln His Trp Leu Pro Lys Val Leu Lys Thr
            100                 105                 110

Tyr Val Glu Lys Tyr Pro Asn Ala Lys Ile Ser Leu Ile Thr Gly Trp
        115                 120                 125

Ser Ser Glu Met Leu Lys Ser Leu Tyr Glu Asp Gln Val His Ile Gly
    130                 135                 140

Ile Ile Arg Gly Asn Pro Glu Trp Lys Gly Arg Lys Asp Tyr Leu Met
145                 150                 155                 160

Thr Asp His Leu Tyr Leu Val Asp Thr Glu Ile Ser Cys Ile Glu Asp
                165                 170                 175

Ile Ala His Thr Glu Arg Pro Phe Ile Gln Phe Lys Ser Asp Ser Thr
            180                 185                 190

Tyr Phe Gln Glu Ile Gln His Trp Trp His Lys Phe Lys Thr Ser
        195                 200                 205

Pro Lys Gln Thr Ile Leu Val Asp Gln Ile Glu Thr Cys Lys Gln Met
    210                 215                 220

Ala Leu His Gly Ile Gly Tyr Ala Ile Leu Pro Ser Val Thr Leu Gln
225                 230                 235                 240

Asn Glu Asp Lys Val Asn Lys Met Pro Leu Leu Asp Met Lys Gly His
                245                 250                 255

Pro Ile Gly Arg Asp Thr Trp Leu Leu Gly Tyr Glu Pro Ala Phe Glu
            260                 265                 270

Leu Lys Gln Val Gln Ala Phe Val Gln Val Ile Lys Asp Met Leu Asp
        275                 280                 285

Gln Glu Asn Pro Phe
    290
```

```
<210> SEQ ID NO 3
<211> LENGTH: 25
<212> TYPE: DNA
<213> ORGANISM: Bacillus subtilis

<400> SEQUENCE: 3
gggagataag aaaaacttat tgata                                          25

<210> SEQ ID NO 4
<211> LENGTH: 24
<212> TYPE: DNA
<213> ORGANISM: Bacillus subtilis

<400> SEQUENCE: 4
tcataagtcg aacttattgt attt                                           24

<210> SEQ ID NO 5
<211> LENGTH: 19
<212> TYPE: DNA
<213> ORGANISM: Bacillus subtilis

<400> SEQUENCE: 5
tgatatttac ttatgtatg                                                 19

<210> SEQ ID NO 6
<211> LENGTH: 16
<212> TYPE: DNA
<213> ORGANISM: Bacillus subtilis

<400> SEQUENCE: 6
ataatgagaa taggct                                                    16

<210> SEQ ID NO 7
<211> LENGTH: 24
<212> TYPE: DNA
<213> ORGANISM: Bacillus subtilis

<400> SEQUENCE: 7
ttataaaaat tgttatgtt cttt                                            24

<210> SEQ ID NO 8
<211> LENGTH: 15
<212> TYPE: DNA
<213> ORGANISM: Bacillus subtilis

<400> SEQUENCE: 8
ataagaaaaa cttat                                                     15

<210> SEQ ID NO 9
<211> LENGTH: 6
<212> TYPE: DNA
<213> ORGANISM: Bacillus subtilis

<400> SEQUENCE: 9 ataagt                                                                6

<210> SEQ ID NO 10
<211> LENGTH: 5
<212> TYPE: DNA
<213> ORGANISM: Bacillus subtilis

<400> SEQUENCE: 10 actta                                                                 5
```

```
<210> SEQ ID NO 11
<211> LENGTH: 14
<212> TYPE: DNA
<213> ORGANISM: Bacillus subtilis

<400> SEQUENCE: 11
tgatatttac ttat                                                         14

<210> SEQ ID NO 12
<211> LENGTH: 6
<212> TYPE: DNA
<213> ORGANISM: Bacillus subtilis

<400> SEQUENCE: 12 acttat                                                                   6

<210> SEQ ID NO 13
<211> LENGTH: 4
<212> TYPE: DNA
<213> ORGANISM: Bacillus subtilis

<400> SEQUENCE: 13 ataa                                                                     4

<210> SEQ ID NO 14
<211> LENGTH: 4
<212> TYPE: DNA
<213> ORGANISM: Bacillus subtilis

<400> SEQUENCE: 14 ataa                                                                     4

<210> SEQ ID NO 15
<211> LENGTH: 4
<212> TYPE: DNA
<213> ORGANISM: Bacillus subtilis

<400> SEQUENCE: 15 ttat                                                                     4

<210> SEQ ID NO 16
<211> LENGTH: 21
<212> TYPE: DNA
<213> ORGANISM: Artificial
<220> FEATURE:
<223> OTHER INFORMATION: Primer

<400> SEQUENCE: 16
aaagtagcgc acgtgcaagt c                                                 21

<210> SEQ ID NO 17
<211> LENGTH: 43
<212> TYPE: DNA
<213> ORGANISM: Artificial
<220> FEATURE:
<223> OTHER INFORMATION: Primer

<400> SEQUENCE: 17
gatctcgacc tgcagcccaa gcagctcttg aagctgcatg tcg                         43

<210> SEQ ID NO 18
<211> LENGTH: 21
<212> TYPE: DNA
<213> ORGANISM: Artificial
```

<220> FEATURE:
<223> OTHER INFORMATION: Primer

<400> SEQUENCE: 18
atcttcatct gtttcaggcg c                                             21

<210> SEQ ID NO 19
<211> LENGTH: 47
<212> TYPE: DNA
<213> ORGANISM: Artificial
<220> FEATURE:
<223> OTHER INFORMATION: Primer

<400> SEQUENCE: 19
gtgtcaaaac gcataccatt ttgaacttta aagacagcga ggtgctg                 47

<210> SEQ ID NO 20
<211> LENGTH: 22
<212> TYPE: DNA
<213> ORGANISM: Artificial
<220> FEATURE:
<223> OTHER INFORMATION: Primer

<400> SEQUENCE: 20
gcttgggctg caggtcgaga tc                                            22

<210> SEQ ID NO 21
<211> LENGTH: 26
<212> TYPE: DNA
<213> ORGANISM: Artificial
<220> FEATURE:
<223> OTHER INFORMATION: Primer

<400> SEQUENCE: 21
gttcaaaatg gtatgcgttt tgacac                                        26

<210> SEQ ID NO 22
<211> LENGTH: 47
<212> TYPE: DNA
<213> ORGANISM: Artificial
<220> FEATURE:
<223> OTHER INFORMATION: Primer

<400> SEQUENCE: 22
gtgtcaaaac gcataccatt ttgaacgagt tggcacagtg aaagccg                 47

<210> SEQ ID NO 23
<211> LENGTH: 23
<212> TYPE: DNA
<213> ORGANISM: Artificial
<220> FEATURE:
<223> OTHER INFORMATION: Primer

<400> SEQUENCE: 23
ctattccttt gtcggttttg ccg                                           23

<210> SEQ ID NO 24
<211> LENGTH: 49
<212> TYPE: DNA
<213> ORGANISM: Artificial
<220> FEATURE:
<223> OTHER INFORMATION: Primer

<400> SEQUENCE: 24
gatctcgacc tgcagcccaa gcgaaataaa cttacaattt gagaaaaac               49

```
<210> SEQ ID NO 25
<211> LENGTH: 21
<212> TYPE: DNA
<213> ORGANISM: Artificial
<220> FEATURE:
<223> OTHER INFORMATION: Primer

<400> SEQUENCE: 25
acatattccc gttatgcatc g                                              21

<210> SEQ ID NO 26
<211> LENGTH: 1962
<212> TYPE: DNA
<213> ORGANISM: Bacillus subtilis

<400> SEQUENCE: 26
acatattccc gttatgcatc gttatattaa ttatttacga gaatttacgg ttttttattc     60
atgaaaaaaa ggaataactc atatgaatga atagattcat attggctgga ggtttagaaa    120
tgggaagaat aaaaaccaag attaccattc tgttagtgct tttgctttta cttgcaggcg    180
gttatatgta cataaatgat attgagctga aggatgttcc gacagcaatt ggacaaacct    240
tgtcctcgga agaagaggaa tacaccatcc aggaatataa agtgacgaaa attgacggct    300
cagagtatca tggagtagca gaaaacggaa cgaaaatcat cttcaacgga aaaaaattaa    360
atcaggattt atctgatata aaagaaggtg acaagattaa ggcttacttc agcaaatcaa    420
agcggatcga cggattaatc aaggttgcaa aagtgaatga ttaaaaaaca tcacctttcg    480
gatcgaaggg tgatgttttg ttttctcaa attgtaagtt tatttctaat ttaaattta    540 tttgacaaaa atgggctcgt gttgtacaat aaatgtagtg ataaggacaa atgaataaag    600
attgtatcct tcggggcagg gtggaaatcc cgaccggcgg tagtaaagca catttgcttt    660
agagtccgtg acccgtgtgc ataagcacgc ggtggattca gtttaagctg aagccgacag    720
tgaaagtctg gatgggagaa ggatgatgag ccgctatgca aaatgtttaa aaatgcatag    780
tgttatttcc tattgcgtaa aatacctaaa gccccgaatt ttttataaat tcggggcttt    840
tttgacggta ataacaaaa gaggggaggg aaacaaatgg aagagtatta tatgaagctg    900
gccttagatc ttgcgaagca gggcgaagga cagaccgaat ccaatccgct cgtcggcgct    960
gttgtcgtaa aggacggaca aattgtcgga atgggcgccc attaaaaata tggtgaagct   1020
catgcagaag ttcatgccat ccatatggct ggagcacatg cagagggtgc cgacatttac   1080
gttacactcg aaccgtgcag ccattacgga aaaacaccgc catgtgcaga attgattatc   1140
aactctggta tcaaaagagt gttcgtggcg atgagagatc ctaatccgct tgtggctgga   1200
agagggatca gcatgatgaa agaagctggc attgaggtaa gggaaggcat cctggcagac   1260
caggcggaga ggctgaatga aaaatttctg cactttatga ggacaggcct tccgtacgtc   1320
acgctaaaag cggctgccag ccttgacggc aagatagcta ccagcacggg tgacagcaaa   1380
tggatcacgt cagaggctgc aagacaggat gctcagcaat acaggaaaac acaccaaagc   1440 atttttagtcg gagttggcac agtgaaagcc gacaatccga gcttaacctg cagactgccg   1500
aatgtaacaa acagccggt tcgggtcata cttgataccg tactctcgat tcctgaggac   1560
gctaaagtga tttgcgatca aatagcgccg acatggattt ttacgacggc acgcgcagac   1620
gaggaaaaga aaaacgct ttcagctttc ggagtgaaca tatttacact tgaaaccgag   1680
cgcattcaaa ttcctgatgt tttgaagatc ctagcggaag aaggcatcat gtcggtgtat   1740
gtggaaggcg gttcagctgt tcacggaagc tttgtcaaag aaggctgttt tcaagaaatc   1800
```

```
atcttctatt ttgcccctaa actaatcgga ggaacgcatg ctcccagctt aatctccggt    1860
gaaggttttc aatcaatgaa agatgtcccc ttattacaat tcactgatat aacccaaatc    1920
ggccgtgata tcaaactgac ggcaaaaccg acaaaggaat ag                       1962
```